US011185007B1

(12) United States Patent
Berg et al.

(10) Patent No.: US 11,185,007 B1
(45) Date of Patent: Nov. 30, 2021

(54) METHODS AND SYSTEMS FOR PRIORITIZING MANAGEMENT OF AGRICULTURAL FIELDS

(71) Applicant: ADVANCED AGRILYTICS HOLDINGS, LLC, Huntington, IN (US)

(72) Inventors: William Kess Berg, Clayton, IN (US); Jon J. Fridgen, Tolono, IL (US)

(73) Assignee: ADVANCED AGRILYTICS HOLDINGS, LLC, Indianapolis, IN (US)

( * ) Notice: Subject to any disclaimer, the term of this patent is extended or adjusted under 35 U.S.C. 154(b) by 0 days.

(21) Appl. No.: 17/100,318

(22) Filed: Nov. 20, 2020

(51) Int. Cl.
*G06K 9/00* (2006.01)
*A01B 79/00* (2006.01)
(Continued)

(52) U.S. Cl.
CPC .......... *A01B 79/005* (2013.01); *A01C 21/005* (2013.01); *G01N 33/24* (2013.01);
(Continued)

(58) Field of Classification Search
CPC ....... G06K 9/0063; G06K 2009/00644; G06K 9/6269; G06K 9/00657; G06K 9/6267; G06K 9/4642; G06K 9/4652; G06K 9/34; G06K 9/40; G06K 2009/6864; G06K 9/4638; G06K 9/4647; G06K 9/50; G06K 9/6227; G06K 9/627; G06Q 50/02; G06Q 10/06393; G06Q 10/063; G06Q 10/109; G06Q 10/04; G06Q 10/06315; G06Q 10/0631; G06Q 10/0635; G06Q 10/06313;
(Continued)

(56) References Cited

U.S. PATENT DOCUMENTS

2019/0050948 A1\* 2/2019 Perry ..................... G06Q 10/04

OTHER PUBLICATIONS

Sahr, Hexagonal Discrete Global Grid Systems for Geospatial Computing, 2011, Archives of Photogrammetry, Cartography and Remote Sensing (Year: 2011).\*

\* cited by examiner

*Primary Examiner* — Alex Kok S Liew
*Assistant Examiner* — Alex Liew
(74) *Attorney, Agent, or Firm* — Marshall, Gerstein & Borun LLP; Randall G. Rueth

(57) ABSTRACT

A computer-implemented method of prioritizing agricultural field management includes training a machine learning model using historical machine data, receiving machine data, classifying the machine data, generating an agricultural prescription instruction set; and performing the agricultural prescription instruction set. A computing system includes a processor and a memory storing instructions that, when executed by the processor, cause the computing system to train a machine learning model using historical machine data, receive machine data, classify the machine data, generate an agricultural prescription instruction set; and perform the agricultural prescription instruction set. A non-transitory computer readable medium includes program instructions that when executed, cause a computer to train a machine learning model using historical machine data, receive machine data, classify the machine data, generate an agricultural prescription instruction set; and perform the agricultural prescription instruction set.

20 Claims, 5 Drawing Sheets

(51) Int. Cl.
*A01C 21/00* (2006.01)
*G06K 9/62* (2006.01)
*G06N 20/00* (2019.01)
*G01N 33/24* (2006.01)

(52) U.S. Cl.
CPC ......... *G06K 9/6256* (2013.01); *G06K 9/6267* (2013.01); *G06N 20/00* (2019.01); *A01C 21/007* (2013.01); *G01N 2033/245* (2013.01)

(58) Field of Classification Search
CPC .. G06Q 10/067; G06Q 10/087; A01B 79/005; A01B 79/02; A01B 15/18; A01B 49/04; A01B 76/00
See application file for complete search history.

METHODS AND SYSTEMS FOR PRIORITIZING MANAGEMENT OF AGRICULTURAL FIELDS

TECHNICAL FIELD

The present disclosure is generally directed to methods and systems for prioritizing management of agricultural fields, and more specifically, for training and operating one or more machine learning models to analyze agricultural field measured values as well as output from mechanistic models to generate and analyze one or more interventions.

BACKGROUND

In conventional precision agriculture, an agricultural analytics company may analyze agricultural field data, and determine that one or more crop fields are lacking in one or more aspects. For example, the company may sample a grower's fields and determine that one or more of the sampled fields are nutrient deficient. However, the analysis may identify hundreds or more fields that are nutrient deficient. The grower may allocate a limited budget for crop treatment that is insufficient to allow full treatment all fields.

Furthermore, the company may provide the grower with treatment recommendations that do not take into account treatment/intervention interactions. For example, treating a field with an agricultural intervention may cause other problems to occur. In some cases, treating a crop field may require a multi-step approach. For example, treating the field to affect one mineralogical aspect (e.g., potassium content) may have interactive/synergistic impacts on other mineralogical aspects (e.g., soil nitrogen).

Still further, existing agricultural treatment techniques provided by the company may be based on regression of historical yield data, rather than yield potential. Therefore, conventional crop management techniques may underperform, relative to the true productive capability of the grower's field.

BRIEF SUMMARY

In one aspect, a computer-implemented method of prioritizing management of an agricultural field includes training a machine learning model by analyzing historical machine data, soils data, and/or topographic data corresponding to one or more agricultural fields; receiving, from an agricultural implement, machine data corresponding to one or more agricultural fields; classifying the machine data corresponding to one or more agricultural fields using a trained random forest model; generating one or more agricultural prescription instruction sets by analyzing the classified machine data using one or more rule sets; and performing the one or more agricultural prescription instruction sets.

In another aspect, a computing system includes a processor and a memory storing instructions that, when executed by the processor, cause the computing system to train a machine learning model by analyzing historical machine data corresponding to one or more agricultural fields; receive, from an agricultural implement, machine data corresponding to one or more agricultural fields; classify the machine data corresponding to one or more agricultural fields using a trained random forest model; generate one or more agricultural prescription instruction sets by analyzing the classified machine data using one or more rule sets; and perform the one or more agricultural prescription instruction sets.

In yet another aspect, a computing system includes a processor and a memory storing instructions that, when executed by the processor, cause the computing system to train a machine learning model by analyzing historical machine data corresponding to one or more agricultural fields; receive, from an agricultural implement, machine data corresponding to one or more agricultural fields; classify the machine data corresponding to one or more agricultural fields using a trained random forest model; generate one or more agricultural prescription instruction sets by analyzing the classified machine data using one or more rule sets; and perform the one or more agricultural prescription instruction sets.

BRIEF DESCRIPTION OF THE FIGURES

The figures described below depict various aspects of the system and methods disclosed therein. It should be understood that each figure depicts one embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

Figure 1:
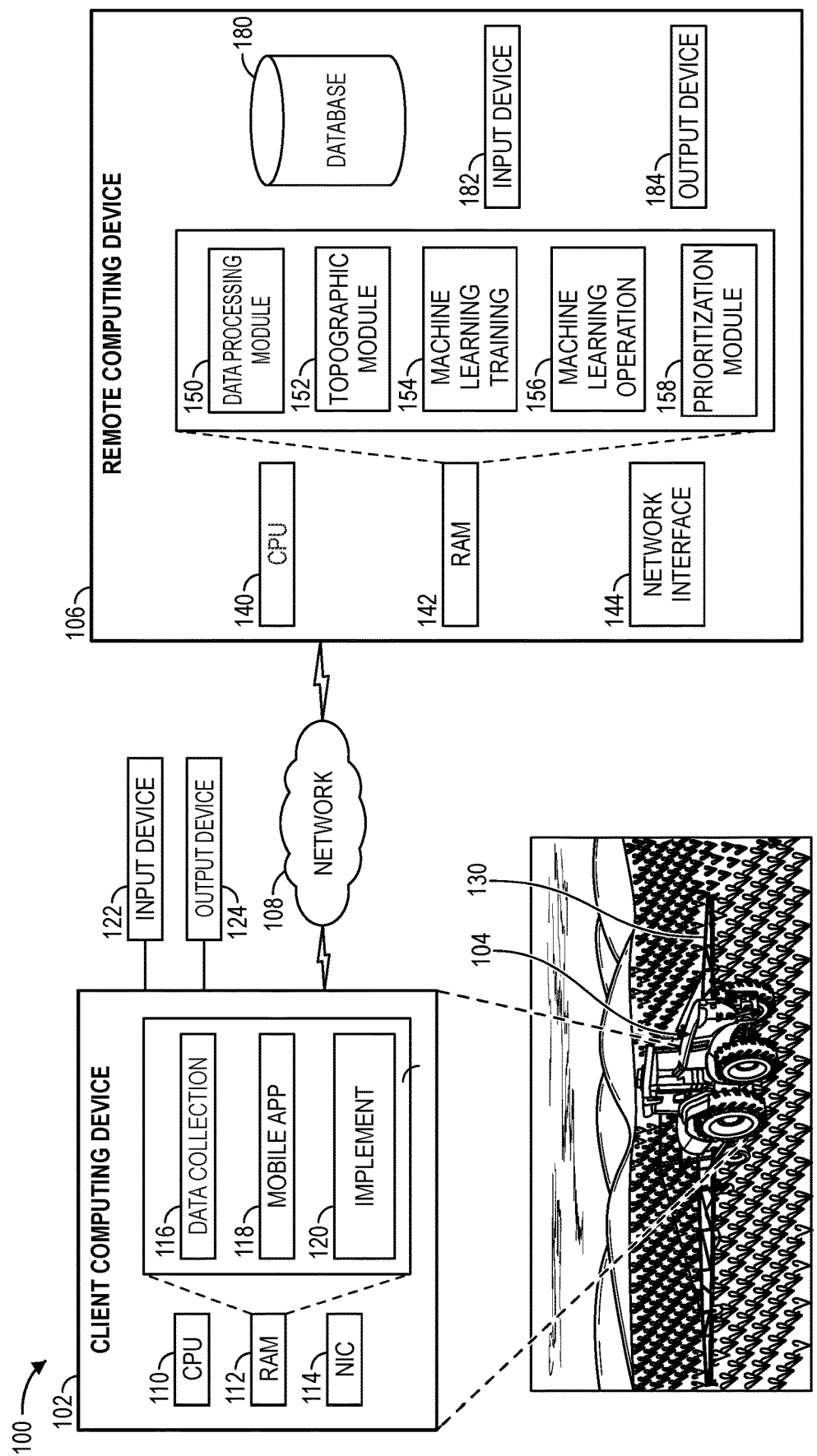
FIG. 1 depicts a computer-implemented method for prioritizing management of an agricultural field, according to one embodiment.

The figures depict preferred embodiments for purposes of illustration only. One of ordinary skill in the art will readily recognize from the following discussion that alternative embodiments of the systems and methods illustrated herein may be employed without departing from the principles of the invention described herein.

DETAILED DESCRIPTION

Overview

The present disclosure is generally directed to methods and systems for prioritizing management of agricultural fields, and more specifically, for training and operating one or more machine learning models to analyze agricultural field measured values to generate a prioritized ranking of agricultural operations.

The present techniques may include collecting machine data, soils data, and/or topographic data from one or more agricultural fields using one or more agricultural equipment implements. In some embodiments, the machine data may be encoded in one or more spatial data files encoded in one or more respective suitable file format, such as a commercial or open source shapefile, a GeoJSON format, a Geography Markup Language (GML) file, etc. Such spatial data files may include one or more layers (i.e., map layers, wherein each layer represents an agricultural characteristic. For example, soil water characteristics may be represented by one or more layer within a shapefile. pH values may be represented in one or more layers, wherein individual pH values corresponding to points within the agricultural field are included in the one or more layers. The individual layer(s) and/or files may be shared between multiple computing devices of an agricultural company, provided or sold to customers, stored in a database, etc.

The machine data may be collected into an historical data set and/or in real-time via a client computing device. The machine data may be stored locally and/or transmitted via an electronic network to a remote computing device for further storage, processing and/or analysis (e.g., for training/operating one or more machine learning model). In some embodiments, the machine data may be collected by a third party (e.g., a government agency or a private industry data vendor). The machine data used for machine learning training/operation may be collected from one grower's agricultural field and used to analyze the productivity of another grower's agricultural field. In some embodiments, the machine data may be collected from a third-party data source. For example, the machine data may be collected directly or indirectly from a farm software platform (e.g., Climate FieldView, John Deere cloud computing, etc.).

The present techniques may include training one or more machine learning (ML) models using stored historical field environmental characterization data (e.g., machine data, soil data, topographic data, etc.). The stored historical data may include data collected from one or more agricultural fields over a period of time (e.g., one week, two months, ten years, etc.). The present techniques may include analyzing machine data using the one or more trained ML models by analyzing collected measured values from an agricultural field to generate one or more interventions. The one or more interventions may include one or more agricultural operations, interventions and/or objectives to improve one or more aspect of the field. The present techniques may include analyzing the generated interventions using a set of rule sets.

In some embodiments, a prioritization algorithm may arrange the agricultural interventions (e.g., in a list, a priority queue wherein each intervention is associated with a respective priority, etc.). In some embodiments, the prioritization algorithm may include instructions for generating a dependency graph including one or more nodes, wherein each node in the dependency graph represents an intervention/objective. In some embodiments, the one or more nodes may be linked to one or more other nodes in the dependency graph by one or more respective sets of edges representing an order in which the interventions/objectives are to be performed. Examples of the dependency graph are provided below.

In some embodiments, the prioritization algorithm may include instructions for arranging/performing the one or more interventions according to one or more aspects of the field (e.g., one or more measured values of the field data, field proximity, etc.), a respective/net cost of the one or more interventions and/or other suitable criteria (e.g., seasonality). In some embodiments, the present techniques may include generating one or more reports, wherein the report includes a graphical/textual representation of the recommended agricultural operations for managing the one or more of the grower's fields.

Exemplary Computing Environment

FIG. 1 depicts an exemplary computing environment 100 in which the techniques disclosed herein may be implemented, according to an embodiment. The environment 100 includes a client computing device 102, an implement 104, a remote computing device 106, and a network 108. Some embodiments may include a plurality of client computing devices 102, a plurality of implements 104, and/or a plurality of remote computing devices 106. Multiple and/or separate networks 106 may communicatively couple different components, such as the client computing device 102 and the implement 104, and/or the client computing device 102 and the remote computing device 106. The components of the environment 100 may be associated with (e.g., leased, owned, and/or operated by), for example, an agrilytics company.

The client computing device 102 may be an individual server, a group (e.g., cluster) of multiple servers, or another suitable type of computing device or system (e.g., a collection of computing resources). For example, the client computing device 102 may be a mobile computing device (e.g., a smart phone, a tablet, a laptop, a wearable device, etc.). In some embodiments the client computing device 102 may be a personal portable device of a user. In some embodiments the client computing device 102 may be temporarily or permanently affixed to the implement 104. For example, the client computing device 102 may be the property of a customer, an agricultural analytics (or "agrilytics") company, an implement manufacturer, etc.

The client computing device 102 includes a processor 110, a memory 112 and a network interface controller (NIC) 114. The processor 110 may include any suitable number of processors and/or processor types, such as CPUs, one or more graphics processing units GPUs). Generally, the processor 110 is configured to execute software instructions stored in the memory 112. The memory 112 may include one or more persistent memories (e.g., a hard drive/solid state memory) and stores one or more sets of computer executable instructions/modules, including machine data collection module 116, a mobile application module 118, and an implement control module 120, as described in more detail below. More or fewer modules may be included in some embodiments. The NIC 114 may include any suitable network interface controller(s), such as wired/wireless controllers (e.g., Ethernet controllers), and facilitate bidirectional/multiplexed networking over the network 108 between the client computing device 102 and other components of the environment 100 (e.g., another client computing device 102, the implement 104, the remote computing device 106, etc.).

The one or more modules stored in the memory 112 may include respective sets of computer-executable instructions implementing specific functionality. For example, in an embodiment, the machine data collection module 116 includes a set of computer-executable instructions for collecting a machine data set from an implement (e.g., the implement 104). The machine data collection module 116 may include a respective set of instructions for retrieving/receiving data from a plurality of different implements, to create the machine data set. For example, a first set of instructions may be for retrieving/receiving machine data from a first tractor manufacturer, while a second set of instructions is for retrieving/receiving machine data from a second tractor manufacturer. In some embodiments, the present techniques may include instructions for collecting soil probe samples.

In still further embodiments, the first and second sets of instructions may, respectively, receive/retrieve data from multiple implements (e.g., a tiller and a harvester) and/or from a mechanistic crop growth model. Of course, some libraries of instructions may be provided by the manufacturers of various implements and/or attachments, and may be loaded into the memory 112 and used by the machine data collection module 116. The data collection module 116 may retrieve/receive machine data from a separate hardware device (e.g., a client computing device 102 that is part of the implement 104) or directly from one or more of the sensors of the implement 104 and/or one or more of the attachments 130 coupled to the implement 104, if any.

The machine data may include any information generated by the client computing device 102, the implement 104 and/or the attachments 130. In some cases, the machine data may be retrieved/received via the remote computing device 106 (e.g., from a third-party cloud storage platform). For example, the machine data may include sensor measurements of engine load data, fuel burn data, draft, fuel consumption, wheel slippage, etc. The machine data may include soil probe information (e.g., organic matter content). The machine data may include one or more time series, such that one or more measured values are represented in a single data set at a common interval (e.g., one-second) or the time series may be comprised of data collected over multiple cropping seasons. For example, the machine data may include a first time series of draft at a one-second interval, a second time series of wheel slippage, etc. The machine data may be location-aware. For example, in some embodiments the client computing device 102 may add location metadata to the machine data, such that the machine data reflects an absolute and/or relative geographic position (i.e., location, coordinate, offset, heading, etc.) of the client computing device 102, the implement 104, and/or the attachments 130 within the agricultural field. The client computing device 102 may add the location metadata at the moment that the client computing device 102 captures the machine data, or at another time. It will also be appreciated by those of ordinary skill in the art that some sensors and/or agricultural equipment may generate machine data that is received by the client computing device 102 that already includes location metadata added by the sensors and/or agricultural equipment. In an embodiment wherein the machine data comprises a time series, each value of the time series may include a respective geographic metadata entry.

The machine data may include further information allowing the client device 106 and other computing components of the environment 100 to uniquely identify the field from which the machine data is collected. For example, location data from a Global Positioning System (GPS) module installed in the client computing device 106 may be added to the machine data. A computing system may analyze the GPS location data to determine the absolute geographic position corresponding to the machine data, and thus, the field to which the GPS location data corresponds. In some embodiments, the machine data may include a unique field identifier (e.g., a universally unique identifier (UUID)) for each respective field. It will be further appreciated by those of ordinary skill in the art that when the machine data is received from a historical archive, the machine data may include historical location data (e.g., the GPS coordinates corresponding to the location from which the historical machine data was captured).

The data collection module 116 may receive and/or retrieve the field environment data and/or machine data via an application programming interface (API) through a direct hardware interface (e.g., via one or more wires) and/or via a network interface (e.g., via the network 108). The data collection module 116 may collect (e.g., pull the machine data from a data source and/or receive machine data pushed by a data source) at a predetermined time interval. The time interval may be of any suitable duration (e.g., once per second, once or twice per minute, every 10 minutes, etc.). The time interval may be short, in some embodiments (e.g., once every 10 milliseconds). The data collection module 116 may include instructions for modifying and/or storing the machine data.

For example, the data collection module 116 may parse the raw machine data into a data structure. The data collection module 116 may add information to the raw machine data (e.g., the field UUID corresponding to the field from which the raw machine data is collected). The data collection module 116 may write the raw machine data onto a disk (e.g., a hard drive corresponding to the memory 112). In some embodiments, the data collection module 116 may transfer the raw machine data, or modified machine data, to a remote computing system/device, such as the remote computing device 106. The transfer may, in some embodiments, take the form of an SQL insert command. For example, the parsed data structure may be stored in an electronic database. In effect, the data collection module 116 performs the function of receiving, processing, storing, and/or transmitting the machine data.

The mobile application module 118 may include computer-executable instructions that display one or more graphical user interfaces (GUIs) on an output device and/or receive user input via an input device. For example, the mobile application module 118 may correspond to a mobile computing application (e.g., an Android, iPhone, or other) computing application of an agrilytics company. In some embodiments, the mobile application module 118 may display a map of the one or more fields of the grower, including respective recommendations corresponding to the one or more fields.

The mobile computing application 118 may be a specialized application corresponding to the type of computing device embodied by the client computing device 102. For example, in embodiments where the client computing device 102 is a mobile phone, the mobile application module 118 may correspond to a mobile application downloaded for iPhone. When the client computing device 102 is a tablet, the mobile application module 118 may correspond to an application with tablet-specific features.

The mobile application module 118 may include instructions for receiving/retrieving mobile application data from the remote computing device 106. In particular, the mobile application module 118 may include instructions for transmitting user-provided login credentials, receiving an indication of successful/unsuccessful authentication, and other functions related to the user's operation of the mobile application. The mobile application module 118 may include instructions for receiving/retrieving, rendering, and displaying visual maps in a GUI. Specifically, the application module 118 may include computer-executable instructions for displaying one or more map layers in the output device 124 of the client computing device 102. The map layers may include spatial and/or geographic information (e.g., a visual indicator corresponding to a prioritization of the one or more fields).

The present techniques significantly improve over conventional techniques in their use of automated data analysis coupled with visualization aspects. Conventionally, an agricultural management company must sift through large volumes of data to determine which management techniques (e.g., agricultural interventions) to apply to a grower's field. Once the laborious work is completed, the agricultural manager is required to attempt to explain any proposed strategies using raw data. The present techniques advantageously analyze the big data sets generated in large-scale farming, and include visualization aspects that allow the agricultural management company (e.g., an agrilytics company) to show the grower which fields or sub-fields are deficient, and how the agrilytics company proposes to improve the fields in a prioritized manner.

The implement control module 120 includes computer-executable instructions for controlling the operation of one or more implements (e.g., the implement 104) and/or the attachments 130. The implement control module 120 may control the implement 104 while the implement 104 and/or attachments 130 are in motion (e.g., while the implement 104 and/or attachments 130 are being used in a farming capacity). For example, the implement control module 120 may include an instruction that, when executed by the processor 110 of the client computing device 102, causes the implement 104 to accelerate or decelerate. In some embodiments, the implement control module 120 may cause one of the attachments 130 to raise or lower the disc arm of a tiller, or to apply more or less downward or upward pressure on the ground. Practically, the implement control module 120 has all of the control of the implement 104 and/or attachments 130 as does the human operator. The implement control module 120 may include instructions for receiving machine data related to soil probes.

The implement control module 120 may include a respective set of instructions for controlling a plurality of implements. For example, a first set of instructions may be for controlling an implement of a first tractor manufacturer, while a second set of instructions is for controlling an implement of a second tractor manufacturer. In another embodiment, the first and second set of instructions may be for, respectively, controlling a tiller and a nutrient applicator. Of course, many configurations and uses are envisioned beyond those provided by way of example. The control module 120 may include computer-executable instructions for executing one or more agricultural prescriptions with respect to the agricultural field. For example, the control module 120 may execute an agricultural prescription that specifies, for a given agricultural field, a path for the implement 104 to follow within the field, and a varying application rate of a chemical (e.g., a fertilizer, an herbicide, a pesticide, etc.) or a seed to apply at various points along the path. The control module 120 may analyze the current location of the implement 104 and/or the attachments 130 in real-time (i.e., as the control module 120 executes the agricultural prescription).

In some embodiments, an input/output (I/O) module may be included in the memory 112. The I/O module may display information received/retrieved from a remote computing device (e.g., the remote computing device 106) and/or process/transmit user input to/from the remote computing device 106. Specifically, the module 10 may include computer-executable instructions for receiving data from an input device of the client computing device 102, for displaying data via the output device 124 of the client computing device 102, and for transmitting the input to a remote computing device (e.g., the remote computing device 104) via the network 108. The I/O module may render one or more graphical user interfaces. For example, the input data may include a request to access a web page, such as a customer information web page, a map layer displayed in the output device 124, etc. Herein, a "user" may be an end user of an application of the agrilytics company (e.g., a customer, an employee, etc.).

In some embodiments, one or more components of the computing device 102 may be embodied by one or more virtual instances (e.g., a cloud-based virtualization service). In such cases, one or more client computing device 102 may be included in a remote data center (e.g., a cloud computing environment, a public cloud, a private cloud, etc.). For example, a remote data storage module (not depicted) may remotely store data received/retrieved by the computing device 102. The client computing device 102 may be configured to communicate bidirectionally via the network 108 with the implement 104 and/or an attachments 130 that may be coupled to the implement 104. The implement 104 and/or the attachments 130 may be configured for bidirectional communication with the client computing device 102 via the network 108.

The client computing device 102 may receive/retrieve data (e.g., machine data) from the implement 104, and/or the client computing device 102 may transmit data (e.g., instructions) to the implement 104. The client computing device 102 may receive/retrieve data (e.g., machine data) from the attachments 130, and/or may transmit data (e.g., instructions) to the attachments 130. The implement 104 and the attachments 130 will now be described in further detail.

The implement 104 may be any suitable powered or unpowered equipment/machine or machinery, including without limitation: a tractor, a combine, a cultivator, a cultipacker, a plow, a harrow, a stripper, a tiller, a planter, a baler, a sprayer, an irrigator, a sorter, an harvester, etc. The implement 104 may include one or more sensors (not depicted) and the implement 104 may be coupled to one or more attachments 130. For example, the implement 104 may include one or more sensors for measuring respective implement values of engine load data, draft sensing, fuel consumption, wheel slippage, etc. The implement 104 may include sensors for taking soil samples (e.g., one or more soil probes). The soil probes may measure soil organic matter, cation exchange capability (CEC), pH, etc. Many embodiments including more or fewer sensors measuring more or fewer machine data implement values are envisioned. The implement 104 may be a gas/diesel, electric, or hybrid vehicle operated by a human operator and/or autonomously (e.g., as an autonomous/driverless agricultural vehicle).

The attachments 130 may be any suitable powered or unpowered equipment/machinery permanently or temporarily affixed/attached to the implement 104 by, for example, a hitch, yoke or other suitable mechanism. The attachments 130 may include any of the types of equipment that the implement 104 may include (e.g., a tiller). The attachments 130 may include one or more sensors (not depicted) that may differ in number and/or type according to the respective type of the attachments 130 and the particular embodiment/scenario. For example, a tiller attachment 120 may include one or more soil probes. It should be appreciated that many attachments 130 sensor configurations are envisioned. For example, the attachments 130 may include one or more cameras. The attachments 130 may include means for sampling soil in situ and/or storing soil samples for later analysis.

The attachments 130 may be connected to the implement 104 via wires or wirelessly, for both control and communications. For example, attachments 130 may be coupled to the client computing device 102 of the implement 104 via a wired and/or wireless interface for data transmission (e.g., IEEE 802.11, WiFi, etc.) and main/auxiliary control (e.g., 7-pin, 4-pin, etc.). The client computing device 102 may communicate bidirectionally (i.e., transmit data to, and/or receive data from) with the remote computing device 106 via the network 108.

The client computing device 102 includes an input device 122 and an output device 124. The input device 122 may include any suitable device or devices for receiving input, such as one or more microphone, one or more camera, a hardware keyboard, a hardware mouse, a capacitive touch screen, etc. The output device 124 may include any suitable device for conveying output, such as a hardware speaker, a computer monitor, a touch screen, etc. In some cases, the input device 122 and the output device 124 may be integrated into a single device, such as a touch screen device that accepts user input and displays output.

The network 108 may be a single communication network, or may include multiple communication networks of one or more types (e.g., one or more wired and/or wireless local area networks (LANs), and/or one or more wired and/or wireless wide area networks (WANs) such as the Internet). The network 108 may enable bidirectional communication between the client computing device 102 and the remote computing device 106, or between multiple client computing devices 102, for example.

The remote computing device 106 includes a processor 140, a memory 142, and a NIC 144. The processor 140 may include any suitable number of processors and/or processor types, such as CPUs and one or more graphics processing units (GPUs). Generally, the processor 140 is configured to execute software instructions stored in the memory 142. The memory 142 may include one or more persistent memories (e.g., a hard drive/solid state memory) and stores one or more sets of computer executable instructions/modules, as discussed below. For example, the remote computing device 106 may include a data processing module 150, a topographic module 152, a machine learning training module 154, a machine learning operation module 156; and a prioritization module 158. The NIC 144 may include any suitable network interface controller(s), such as wired/wireless controllers (e.g., Ethernet controllers), and facilitate bidirectional/multiplexed networking over the network 106 between the remote computing device 106 and other components of the environment 100 (e.g., another remote computing device 106, the client computing device 102, etc.).

The one or more modules stored in the memory 142 may include respective sets of computer-executable instructions implementing specific functionality. For example, in an embodiment, the data processing module 150 includes computer-executable instructions for receiving/retrieving data from the client computing device 102, the implement 104, and/or the attachments 130. For example, the data processing module 150 may include instructions that when executed by the processor 140, cause the remote computing device 106 to receive/retrieve machine data. The data processing module 150 may include further instructions for storing the machine data in one or more tables of the database 180. The data processing module 150 may store raw machine data, and/or processed data. The data processing module 150 may include instructions for processing the raw machine data to generate processed data. For example, the data processing module 150 may convert the raw machine data to processed data using data types data of a programming language (e.g., R, C #, Python, JavaScript, etc.). The data processing module 150 may include instructions for validating the data types present in the processed data. For example, the data processing module 150 may verify that a value is present (i.e., not null) and is within a particular range or of a given size/structure. In some embodiments, the data processing module 150 may transmit processed data from the database 180 in response to a query, or request, from the client computing device 102. The data processing module 150 may transmit the processed data via HTTP or via another data transfer suitable protocol.

The topographic module 152 may include instructions for retrieving and/or providing geographic data to other modules in the remote computing device 106. For example, the topographic module 152 may retrieve/receive geographic data corresponding to a plurality of fields under the management of the agrilytics company (e.g., the fields shown below). The geographic data may include machine data corresponding to the current state of the fields and/or historical field states. It will be appreciated by those of skill in the art that historical field states for a first customer may be used to train a model used to generate predictions for a second customer. Similar fields, in terms of soil composition, may be compared to generate field management decisions for different customers. When ownership of a field changes hands from a first customer to a second customer, the historical field data of the first customer may be analyzed to train and/or operate the machine learning model to generate field management decisions for the second customer.

By analyzing the geographic data, the topographic module 152 may determine differences between the current and past state of the fields. The topographic module 152 may include instructions for receiving/retrieving elevation data from public sources, such as the United States Geological Survey (USGS) National Elevation Dataset (NED) database. The topographic module 152 may store the elevation data in the database 180. In some embodiments, the elevation data may be stored in a two-dimensional (2D) or three-dimensional (3D) data format, depending on the embodiment and scenario.

The topographic module 152 may include computer-executable instructions for generating one or more map layers and/or one or more geospatial data files (e.g., shapefiles). The topographic module 152 may store the generated map layers and/or geospatial files in the database 180, or in the memory 142. The topographic module 152 may provide the geospatial files and/or map layers to other components of the environment 100, such as the client computing device 102. Specifically, the topographic module 152 may include an API endpoint that allows the mobile application module 118 to submit a query/request to receive/retrieve one or more geospatial files and/or one or more map layers via the network 108. It will be appreciated by those of ordinary skill in the art that the topographic module 152 may use existing standardized and/or proprietary software libraries to generate the maps and/or shape files. Further, the topographic module 152 may combine one or more data sets from the database 180 into a single map layer/geospatial file, or into multiple respective map layers. For example, the topographic module 152 may generate a composite geospatial data file that includes a first map layer representing a set of one or more values corresponding to a first field in the plurality of agricultural fields, a second map layer representing a set of one or more values corresponding to a second field in the plurality of agricultural fields, etc.

When, for example, the mobile application module 118 retrieves the composite geospatial data file, the mobile application module 118 may display the first map layer and/or the second map layer either independently or in an overlay view. In this way, the user is able to attain a clear visualization of the values corresponding to the plurality of fields managed by the agrilytics company. The field data collected, stored, processed and/or retrieved by the topographic module 152 may be accessed by other components/ modules of the environment 100 (e.g., the machine learning training module 154 and/or the machine learning operation module 156).

The machine learning training module 154 is generally configured to load, create, train, and/or store ML models for use by the remote computing device 106 and/or the client computing device 102. For example, the ML training module 154 may include instructions for training a deep learning artificial neural network model by analyzing labeled machine data.

In general, the ML training module 154 may train models by, inter alia, establishing a network architecture, or topology, and adding one or more layers that may be associated with one or more respective activation functions (e.g., a rectified linear unit, softmax, etc.), loss functions and/or optimization functions. Multiple different types of artificial neural networks may be employed, including without limitation, recurrent neural networks, convolutional neural networks, and deep learning neural networks. Data sets used to train the artificial neural network(s) may be divided into training, validation, and testing subsets; these subsets may be encoded in an N-dimensional tensor, array, matrix, or other suitable data structures. Training may be performed by iteratively training the network using labeled training samples. Training of the artificial neural network may produce byproduct weights, or parameters which may be initialized to random values. The weights may be modified as the network is iteratively trained, by using one of several gradient descent algorithms, to reduce loss and to cause the values output by the network to converge to expected, or "learned", values.

A mechanistic crop growth model may be one in which the physiological processes of one or more crops (e.g., photosynthesis, respiration, etc.) are expressed in relation to crop attributes (e.g., plant height). Mechanistic models may describe the behavior of a crop in terms of the crop's lower level attributes. The present techniques may input data (e.g., machine data) describing a given plant's lower level attributes into a trained mechanistic crop growth model in order to generate a prediction of crop behavior and yield. A non-limiting example of a mechanistic crop model that may be used in conjunction with the present invention is the AquaCrop mechanistic model, published by the Food and Agriculture Organization (FAO) of the United Nations. It will be appreciated by those of ordinary skill in the art that many different models may be suitable for use with the present techniques.

In an embodiment, a regression neural network may be selected which lacks an activation function, wherein input data may be normalized by mean centering, to determine loss and quantify the accuracy of outputs. Such normalization may use a mean squared error loss function and mean absolute error. The artificial neural network model may be validated and cross-validated using standard techniques such as hold-out, K-fold, etc. In some embodiments, multiple artificial neural networks may be separately trained and operated, and/or separately trained and operated in conjunction.

The ML training module 154 may train a processor or a processing element using supervised or unsupervised machine learning, and the machine learning module may employ a neural network, which may be a convolutional neural network, a deep learning neural network, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs. For example, a deep learning artificial neural network may be trained using historical machine data to generalize about previously unseen machine data. The ML training module 154 may store the trained models in the memory 142 and/or the database 180. The ML training module 154 may transmit the trained ML models to another component of the computing environment 100 (e.g., the client computing device 102).

The machine data may be collected via a client computing device and stored locally and/or transmitted via an electronic network to a remote computing device for further storage, processing and/or analysis (e.g., for training one or more machine learning model). In some embodiments, the machine data may be collected by a third party (e.g., a government agency or a private industry data vendor).

The present techniques may include training one or more machine learning (ML) models using stored historical machine data. The stored historical machine data may include machine data collected from one or more agricultural fields over a period of time (e.g., one week, two months, ten years, etc.). The present techniques may include analyzing machine data using the one or more trained ML models by analyzing collected measured values from an agricultural field to generate a ranking. The ranking may include one or more agricultural operations, interventions and/or objectives to improve one or more aspect of the field.

The machine learning operation module 156 may load a model (e.g., a deep learning model) trained by the ML training module 154 from the memory 142 or another location. For example, the ML operation module 156 may load a trained ML model and pass a series of parameters (e.g., a matrix of point data values corresponding to a field). The ML operation module 156 may receive from the trained deep learning model a copy of the matrix wherein each point data value is associated with a category/class label. The matrix including the respective point data labels may be stored in the memory of the remote computing device 106 or in another location (e.g., in an electronic database of the remote computing device 106). The ML operation module 156 may feed the matrix into the trained ML model and receive one or more outputs from the trained ML model. The ML outputs may correspond to a set of one or more agricultural interventions or objectives (e.g., a nutrient application rate, a variable-rate seeding rate, etc.). When the matrix is fed into the trained ML model, the ML model may adjust the weights of the artificial neural network based on the matrix.

The prioritization module 158 may include one or more sets of computer-executable instructions for arranging agricultural interventions (e.g., in a list, a priority queue wherein each intervention is associated with a respective priority, etc.). In some embodiments, the prioritization algorithm may include instructions for generating a dependency graph including one or more nodes, wherein each node in the dependency graph represents an intervention/management objective. In some embodiments, the one or more nodes may be linked to one or more other nodes in the dependency graph by one or more respective sets of edges representing an order in which the interventions/objectives are to be performed. Examples of the dependency graph are provided below.

In some embodiments, the prioritization module 158 may arrange the agricultural interventions (e.g., in a list, a priority queue wherein each intervention is associated with a respective priority, etc.). In some embodiments, the prioritization module 158 may include instructions for generating a dependency graph including one or more nodes, wherein each node in the dependency graph represents an intervention/objective. In some embodiments, the one or more nodes may be linked to one or more other nodes in the dependency graph by one or more respective sets of edges representing an order in which the interventions/objectives are to be performed. In some embodiments, the prioritization module 158 may include instructions for arranging/performing the one or more interventions according to one or more aspects of the field (e.g., one or more measured values of the machine data, field proximity, etc.), a respective/net cost of the one or more interventions and/or other suitable criteria (e.g., seasonality). In some embodiments, the present techniques may include generating one or more reports, wherein the report includes a graphical/textual representation of the recommended agricultural operations for managing the one or more of the grower's fields.

The remote computing device 106 may further include one or more database 180, an input device 182, and an output device 184. The database 180 may be implemented as a relational database management system (RDBMS) in some embodiments. For example, the data store 140 may include one or more structured query language (SQL) database, a NoSQL database, a flat file storage system, or any other suitable data storage system/configuration. In general, the database 180 allows the client computing device 102 and/or the remote computing device 106 to create, retrieve, update, and/or retrieve records relating to performance of the techniques herein. For example, the database 180 may allow the client computing device 102 to store information received from one or more sensors of the implement 104 and/or the attachments 140. The database 180 may include a Lightweight Directory Access Protocol (LDAP) directory, in some embodiments. The client computing device 102 may include a module (not depicted) including a set of instructions for querying an RDBMS, an LDAP server, etc. For example, the client computing device 102 may include a set of database drivers for accessing the database 180 of the remote computing device 106. In some embodiments, the database 180 may be located remotely from the remote computing device 104, in which case the remote computing device 104 may access the database 180 via the NIC 112 and the network 106.

The input device 182 may include any suitable device or devices for receiving input, such as one or more microphone, one or more camera, a hardware keyboard, a hardware mouse, a capacitive touch screen, etc. The input device 182 may allow a user (e.g., a system administrator) to enter commands and/or input into the remote computing device 106, and to view the result of any such commands/input in the output device 184.

The output device 184 may include any suitable device for conveying output, such as a hardware speaker, a computer monitor, a touch screen, etc. The remote computing device 106 may be associated with (e.g., leased, owned, and/or operated by) an agrilytics company. As noted above, the remote computing device 106 may be implemented using one or more virtualization and/or cloud computing services. One or more application programming interfaces (APIs) may be accessible by the remote computing device 106.

In operation, the client computing device 102 may collect machine data from the one or more fields using the implement 104 and/or the attachments 130. The data collection module 116 may receive/retrieve machine data at an interval or continuously, and store the data locally (e.g., in the memory 112) and/or transmit the machine data via the network 108 to the remote computing device 106 for remote storage (e.g., in the database 180). The mobile application 118 may include instructions for modifying the collection of the machine data by, for example, pausing collection, modifying the route of the implement 104, controlling one or more attachments 130, etc.

By the time the implement collects machine data, the remote computing device 106 may have already trained one or more machine learning models by using the machine learning training module 154 to analyze historical stored machine data. The training may include analyzing the machine data collected by the implement 104, or other stored machine data. For example, in some cases the historical machine data may be collected on the previous day, or a prior year. The historical machine data may correspond to data from any agricultural field. Once the machine learning models are trained, the machine learning operation module 156 may analyze machine data in real-time using the trained machine learning models.

For example, the machine learning operation module 156 may receive/retrieve additional machine data from the implement module 120 of the client computing device 102. The machine learning operation module 156 may provide some of the additional machine data to the trained machine learning model to generate one or more recommended interventions with respect to an agricultural field. The one or more recommended interventions may apply to the entire field, and/or a subset of the field. In some cases, the interventions may be associated with hexagonal subdivisions of the field (e.g., field-level hexagrids). For example, the field may be subdivided into 8.5-meter hexagonal grids.

In some embodiments, the trained machine learning model may be located in the client computing device, allowing the present techniques to advantageously provide immediate feedback based on analyzing the additional machine data, without the need to transmit large volumes of machine data via the network 108. The trained machine learning model may require comparatively less computing power to operate, in relation to the amount of computing power required for training the trained machine learning model. Therefore, in some embodiments, the client computing device 102 may be a thin device, such as a smart phone, tablet, laptop, etc. The client computing device 102 may be equipped with memory 112 sufficient to store large data sets (e.g., terabytes or more), allowing big data computing approaches to be used in real-time, even in more remote areas that may lack strong network connectivity.

In some embodiments, the machine learning model 306 may be trained using labeled data. Training the machine learning model 306 may generate network weights that may be stored, for example in the database 180. The machine learning model 306 may be implemented as an artificial neural network, for example. The machine learning model 306 may include one or more random forest tree networks for identifying one or more interventions that should be applied to the field from which the machine data is collected, for improving yield, productivity, etc.

The random forest modeling may include classifying each field at the hexagrid, or cellular, level. Specifically, the machine learning model 306 may be a random forest model that classifies each hexagrid of a field using a random forest model. The random forest model may consist of a plurality of decision trees, each of which independently classifies each hexagrid according to pre-determined criteria (e.g., pH, CEC, organic matter, etc.). Once the plurality of decision trees has independently classified a respective hexagrid, the present technique may choose a classification output based on an ensemble or voting technique. In this way, the random forest method may classify input data corresponding to each hexagrid within the agricultural fields. Once each hexagrid has been classified, the present techniques may aggregate the results of the individual hexagrid classifications. In another embodiment, the random forest tree may classify data at the field level.

The prioritization module 158 may map the interventions generated by the machine learning module using a dependency graph. The prioritization module 158 may use the dependency graph to determine an initial ordering in which to apply the interventions, noting for example that to modify one (e.g., sulfur) may affect another (e.g., pH). The prioritization module 158 may simulate effects of applying one or more interventions, and further analyze machine data in view of the simulated effects. For example, the prioritization module 158 may simulate the effect of adding nitrogen by modifying the machine data set, generating a simulated data set. The prioritization module 168 may then cause the machine learning operation module 156 to analyze the machine data set to generate first output, and the simulated data set to generate second output. The prioritization module 158 may compare the first output and e second output to determine a priority of application of the one or more crop interventions.

The prioritization module 158 may generate one or more agricultural prescription instruction sets for carrying out the interventions. For example, an increase Sulfur instruction set may apply certain nutrients to the field. In some embodiments, the agricultural prescription instruction sets may accept one or more intervention parameters. For example, the prescription instruction set may accept a current Sulfur concentration, a target Sulfur concentration, a crop identifier and a field size expressed in square meters. The prescription instruction set calculate a rate at which to apply the intervention to increase the Sulfur concentration to the target concentration, for example, or the pH to the target pH, in accordance with the crop identifier and the field size.

Exemplary Plurality of One or More Managed Agricultural Fields

Figure 2:
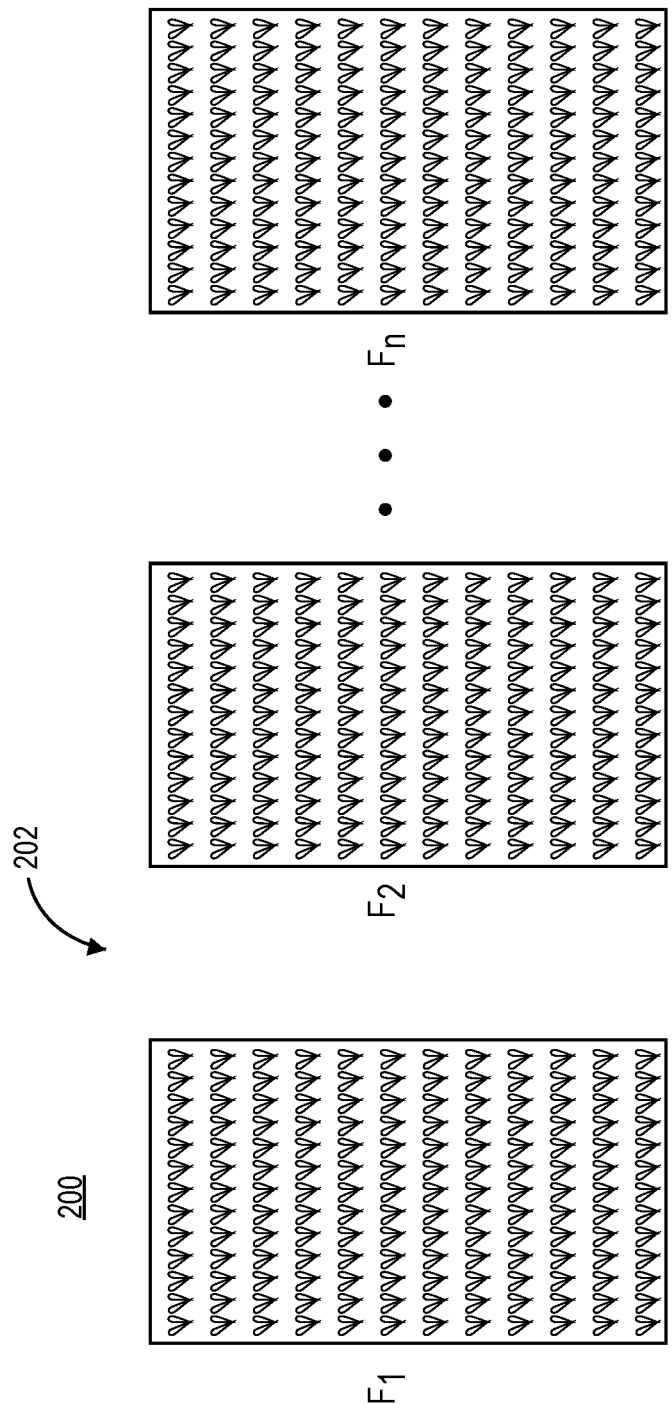
FIG. 2 depicts an exemplary block diagram of a plurality of managed agricultural fields, according to one embodiment.

FIG. 2 depicts an exemplary block diagram 200 of a plurality of managed agricultural fields 202. The managed fields 202 are indexed as $F_1$, $F_2$ through $F_n$, where n may be any positive integer. Each of the managed fields 202 may correspond, respectively, to the field depicted within the environment 100 of FIG. 1, from which the implement 104 collects machine data. The data processing module 150 and the topographic module 152 may perform their respective functions as discussed above independently with respect to each of the managed fields 202.

The managed fields 202 may be associated with one or more grower in a many-to-one, one-to-many and/or many-to-many relationship. The managed fields 202 may be associated with a field identifier (e.g., each may correspond to its own UUID). The fields may correspond to owner information. For example, the field F1 may be owned by a first grower, while the field F2 is owned by a second grower, and so on. In some embodiments, a single grower may own more than one of the managed fields 202. In some embodiments, multiple growers may own one or more of the managed fields 202. The relationships between field/grower may be represented in any suitable way, including as data objects in a relational database.

Figure 3:
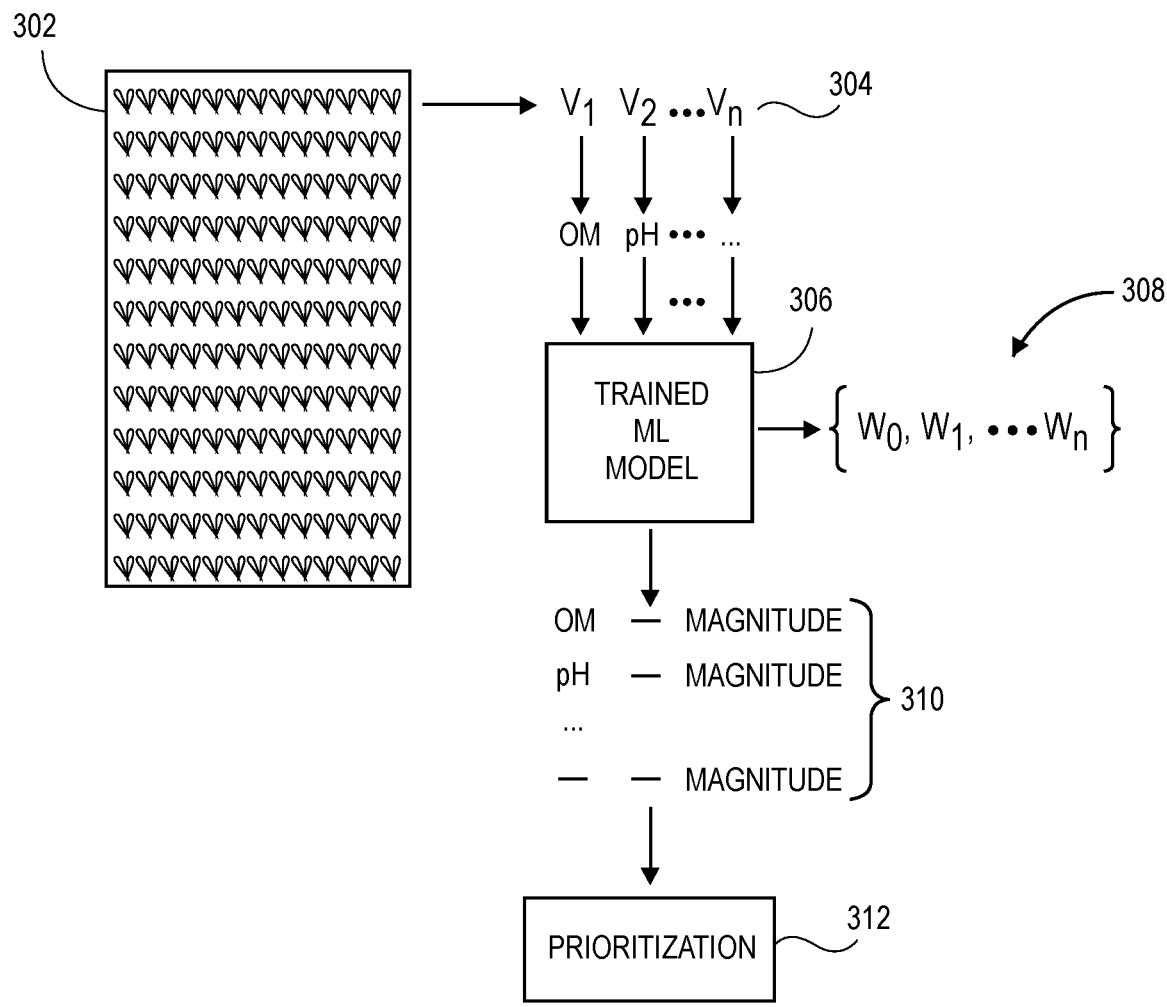
FIG. 3 depicts an exemplary combined data flow and method flow diagram depicting training and operating one or more machine learning models to prioritize management of an agricultural field by analyzing collected measured values from an agricultural field to generate a ranking, according to one embodiment and scenario.

FIG. 3 depicts an exemplary combined data flow and method flow diagram 300 depicting training and/or operating one or more machine learning models to prioritize management of one or more agricultural fields by analyzing collected measured values from the agricultural fields to generate one or more agricultural interventions or objectives, according to one embodiment and scenario. The diagram 300 includes an agricultural field 302 that may include one or more crop plantings (e.g., corn, soybean, wheat, etc.). The agricultural field 302 may correspond to one of the plurality of managed agricultural fields 202 of FIG. 2, for example.

The diagram 300 may include a plurality of values 304, including individual measurement values V1 through Vn. Each of the plurality of values 304 may correspond to machine data collected by the implement 104 of FIG. 1, in some embodiments. The plurality of values 304 may correspond to individual time steps in a time series of machine data collected by the implement 104, for example. Each row/column point of the field 302 may include multiple instances of the plurality of values 304. The multiple instances of the plurality of values may be collected from hexagrid subdivisions of the field 302, in some embodiments. The hexagrid subdivisions may be hexagonal shapes used to subdivide the field of fixed or variable dimensions. The plurality of values may correspond to one or more respective agricultural measurements (e.g., organic matter, nutrient concentrations, pH, cation exchange capacity, base saturation, etc.). The agricultural measurements may be determined by instructions executing in the client computing device 102 (e.g., in the data collection module 116). The plurality of values 304 may be stored in the client computing device 102 and/or transmitted to the remote computing device 106, for example via the network 108.

The plurality of values 304 may be received/retrieved by a trained machine learning model 306, in some embodiments. The trained machine learning model 306 may be executing in the machine learning operation module 156 of FIG. 1, as discussed above, for example. The trained machine learning model 306 may be a model trained, for example, using historical machine data labeled using crop yield data, field potential productivity, and/or other labeled data. The prior training may determine a plurality of weights 308 including weights $W_1$ through $W_n$, where n is any positive integer. When the trained machine learning model 306 retrieves/receives the plurality of values 304, the trained machine learning model 306 may be pre-initialized using the plurality of weights 308 (e.g., by the machine learning operation module 156 of FIG. 1). The initialized and trained machine learning model 306 may analyze the plurality of values 304 and emit a set of one or more output values 310. When the trained machine learning model is a random forest model, the weights $W_1$ through $W_n$ may correspond to individual decision trees of the trained machine learning model, in some embodiments.

The set of output values 310 may correspond to the plurality of values 304, in some embodiments. For example, the number of output values 310 may be the same as the plurality of values 304. In some embodiments, a single output value may be generated. The topology and configuration of the trained machine learning model 306 may determine the output parameters. The output 310 may correspond to a ranking of respective interventions.

In some embodiments, the trained machine learning model 306 may be trained to simulate an effect, based on a first agricultural attribute of a field, of applying an agricultural intervention on a second agricultural attribute of a field. For example, the machine learning training module 154 may determine that a soil nitrate value is too low based on historical optimal nitrate values for yield. The trained machine learning model 306 may determine that an intervention of variable-rate seeding is indicated based on the training using the labeled historical training data. The machine learning model 306 may output a list of one or more additional recommended interventions to increase yield and/or to reach potential productivity (e.g., a secondary intervention, a tertiary intervention, etc.).

In some embodiments, the trained machine learning model 306 may be implemented as a random forest model that outputs variable importance for a plurality of potential interventions. The random forest algorithm may be adjusted to optimize one or more factors (e.g., atomic absorption, nitrogen loss, potential productivity, etc.) in some embodiments. The outputs of the trained machine learning model 306 may include classifications at a hexagrid level. Another module (e.g., a prioritization module), may analyze each of the hexagrid-level classifications of a given field to generate a field-level aggregated classification, or ranking.

The diagram 300 may include a prioritization module 312. The prioritization module 312 may include computer-executable instructions for analyzing the output of the trained machine learning model 306. For example, the prioritization module may include a further trained machine learning model and/or rule sets for ordering interventions, as depicted below. In some embodiments, the prioritization module 312 may include instructions for simulating the application of one or more crop product interventions, and for feeding machine data into the trained machine learning model 306 based on simulated values.

The prioritization module 312 may include instructions for analyzing the economic cost of applying one or more interventions to crops in relation to an intervention budget. The intervention budget may be provided by the user of the remote computing system via the input device 182, for example. In some embodiments, the user may provide budget information via the input device 122 of the client computing device 102. For example, the prioritization module 312 may collect recommended interventions from the trained machine learning model 306 with respect to a plurality of fields (e.g., the plurality of managed agricultural fields 202 of FIG. 2). The prioritization module 312 may analyze each of the fields to determine how much of an intervention (e.g., the amount of phosphorus) to apply to each of the managed fields. The rule sets may include crop product application rules, such as a dynamic programming-based algorithm.

Figure 4:
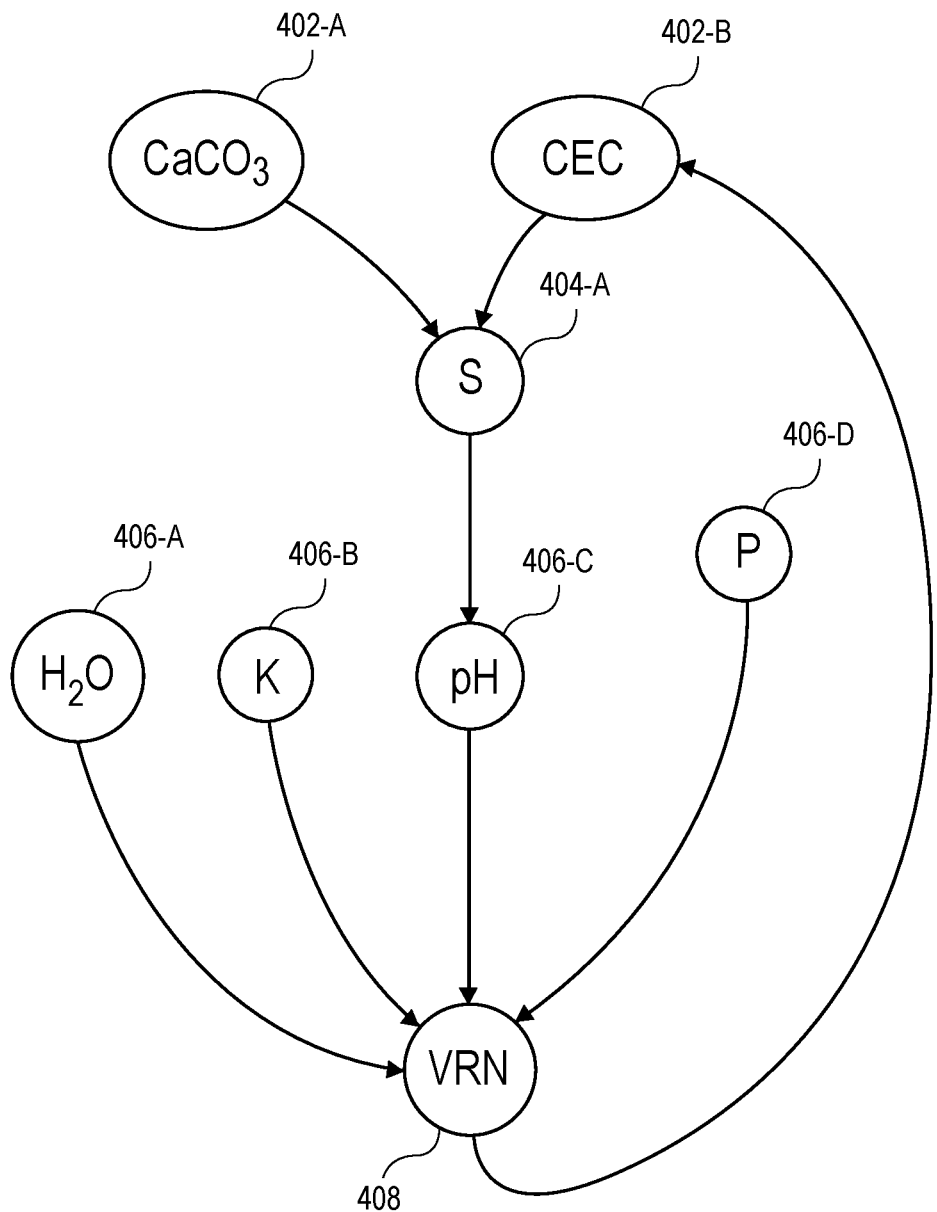
FIG. 4 depicts an exemplary dependency diagram depicting a plurality of prioritized field measurements, according to one embodiment.

FIG. 4 depicts an exemplary diagram of a dependency graph 400 depicting a plurality of prioritized field measurements, according to one embodiment. The dependency graph 400 may include a plurality of hierarchical weighted factors for determining the order of application of products to the plurality of agricultural fields. For example, in an embodiment, the trained machine learning model 306 may determine that improving plant available soil water capacity by modifying pore space and/or water infiltration will lead to increased yields. The dependency graph may encode information, for example that increasing pore space may lead to an increase in plant available water. Therefore, the prioritization module 312 of FIG. 3 may determine that pore space must be modified before measuring/addressing other crop management (e.g., tile drainage, irrigation, foliar application of nutrients, etc.).

In the depicted example of FIG. 4, the dependency graph 400 includes a plurality of layers including a first hierarchical layer that includes a calcium carbonate node 402-A and a cation exchange capability node 402-B. The first hierarchical layer is linked to a second hierarchical layer including a sulfur node 404-A. The second hierarchical layer is linked to a pH node 406-C, which is included in a third hierarchical layer also comprising a water node 406-A, a potassium node 406-B, and a phosphorus node 406-D. Each of the nodes within the third hierarchical layer may be linked to a fourth hierarchical node 408, representing a variable-rate nitrogen application intervention.

By analyzing the plurality of layers of the dependency graph 400, the priority module 312 may map the output generated by the trained machine learning module 306 (e.g., one or more recommendations) for a given field to determine an order in which to apply the recommended interventions. In some embodiments, the dependency graph 400 may be used to generate a customer management priority report, depicting importance of variables generated by, for example, a random forest algorithm along with an order in which to apply each intervention. The reports may be generated by prioritization module 312, for example, with respect to a plurality of managed fields (e.g., the fields 202 of FIG. 2).

Exemplary Computer-Implemented Methods

Figure 5:
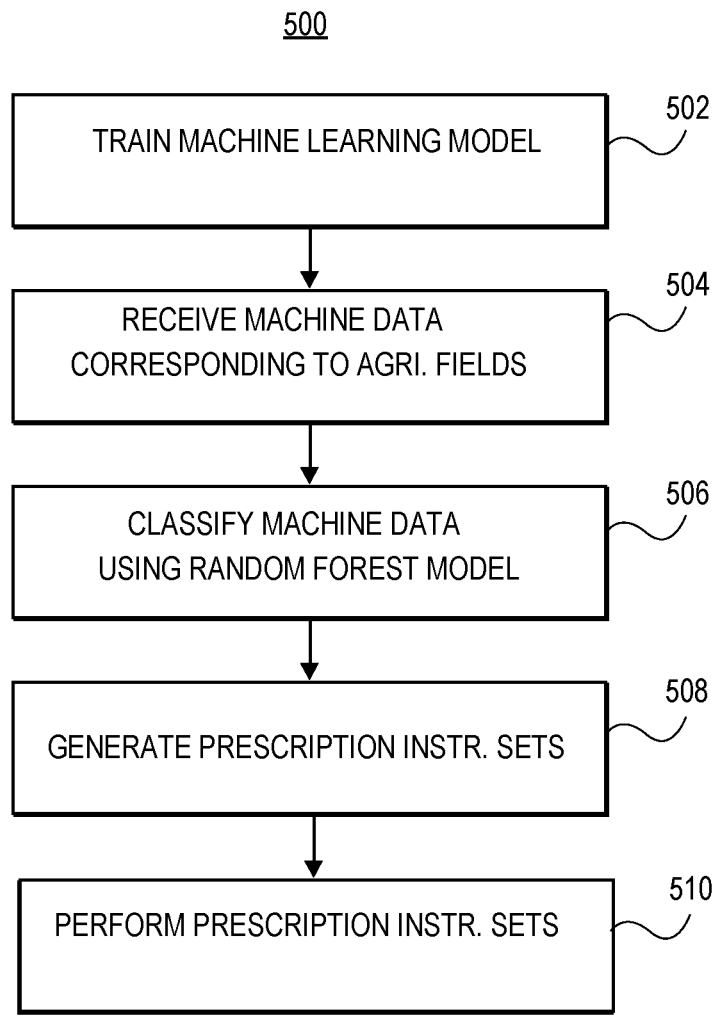
FIG. 5 depicts an exemplary computer-implemented method for prioritizing management of agricultural fields, according to one embodiment and scenario.

FIG. 5 depicts an exemplary computer-implemented method 500 for prioritizing management of agricultural fields, according to one embodiment and scenario.

The method 500 may include training a machine learning model, wherein the training generates a set of weights (block 502). The machine learning training module 154 may perform the training, in some embodiments. Historical machine data may be used to train the machine learning model. The historical machine data may include, for example, a plurality of variables corresponding to the agricultural field, such as the agricultural field 302 depicted in FIG. 3. The plurality of variables may correspond to aspects of the field, such as organic matter, pH, cation exchange capability, topography, etc. The plurality of values may be input as a single tensor representing the entire field, or as multiple individual tensors corresponding to respective hexagrids within the field.

In some embodiments, the historical machine data may include labels corresponding to aspects of interest to the grower, such as yield, potential productivity, etc. Once the model is trained, a set of weights may be associated with the trained machine learning model. The weights allow the machine learning model to be initialized by the machine learning operation module 156 of FIG. 1, for example, without the need to re-train. The machine learning training module 156 may train a random forest model, in some embodiments. For example, the random forest model may be provided with training data for classifying one or more hexagrids of an agricultural field according to multiple criteria (e.g., pH, cation exchange capacity, organic matter content, topography, etc.).

The method 500 may include receiving, from an agricultural implement, machine data corresponding to one or more agricultural fields (block 504). Collecting the machine data may include the implement 104 colleting a soil probe sample that is tagged with a geographic position. The soil probe sample may be analyzed in situ or later, in an asynchronous process (e.g., by the data processing module 150 of FIG. 1). The machine data may include measured values that correspond to the plurality of variables in the historical machine data or to other values.

The machine learning operation module 156 may analyze the one or more agricultural fields using the trained random forest model to classify the respective one or more fields by one or more of the criteria (block 506). For example, one classification outcome may be a nutrient deficiency. The classification may be performed at a field and/or sub-field (e.g., hexagrid) level. The random forest model may analyze each of the measured values of a field/sub-field according to the training, to generate one or more respective classifications. Once the machine learning operation module 156 classifies each hexagrid into one or more category, another module may analyze the classifications.

The method 500 may include generating one or more agricultural prescription instruction sets by analyzing the classified machine data using one or more rule sets (block 508). For example, with reference to FIG. 2, the trained random forest classifier may classify the soil of $F_1$ and $F_2$ as low in pH and low in nitrogen. A first rule set may be applied that generates an instruction set for an agricultural prescription to add nitrogen to the soil. A second rule set may be applied that generates an instruction set for an agricultural prescription to add lime to the acidic soil. For an alkaline soil, the rule sets may generate an instruction set for adding sulfur or gypsum to the soil. In some cases, the rule sets may determine that adding an acidity adjustment treatment and a fertilizer treatment simultaneously can be done without any significant interactions. However, as discussed above with respect to FIG. 4, in some embodiments, the rule sets may be more complex and must resolve one or more interdependencies between objectives and/or treatments.

In such cases, the method 500 may include simulating one or more effect of one or more agricultural treatments with respect to the field. For example, the simulation may include using a mechanistic crop growth model, as discussed above. In still further embodiments, the method 500 may include generating the one or more agricultural prescription instruction sets by analyzing the economic cost for performing the one or more treatments as indicated by the rule sets. In some embodiments, the rule sets may determine that the highest impact on yield can be had by performing a particular treatment (e.g., pH adjustment) and that doing so for the most acidic fields among the group of fields first is the most economically impactful strategy. The rule sets may include instructions for simulating the economic impact of different interventions.

The method 500 may include performing the one or more agricultural prescription instruction sets (block 510). For example, the method 500 may include displaying the prescription in a mobile application downloaded from an application store, such as Senio for the Apple iOS platform. The prescription may include one or more maps, a last-scouted time, and other information pertaining to the field (e.g., plant population, growth stage, etc.). In some embodiments, the user (e.g., a grower, a field manager, etc.) may view one or more agricultural fields and simulate the application of the one or more agricultural prescription instruction sets to the field. The mobile application may include an indication of an order in which the agricultural prescription instruction sets will be applied to the field, and visual indications of which segments/sub-portions (e.g., hexagrids) of the field the prescription instruction sets will apply to.

For example, the method 500 may include generating a time-ordered priority list of management actions within a portion of an enterprise report based on the one or more agricultural prescription instruction sets. The enterprise report may include a list of each of the agricultural prescription instruction sets to be performed on a field-by-field basis. For example, each page of the enterprise report may include one of the fields 202 of FIG. 2, along with a prioritized list of agricultural interventions that will be performed according to the agricultural prescription instruction sets. The method 500 may include combining the agricultural prescription instruction sets into an agricultural prescription. In some embodiments, the agricultural prescription may be a file or data object. The method 500 may include loading the agricultural prescription into the memory of an agricultural implement, such as the implement 104 of FIG. 1. The agricultural prescription may be stored and executed in the implement, for example by the implement control module 120 of FIG. 1. Executing the agricultural prescription, and/or agricultural prescription instruction sets, may include performing any operations supported by the implement (e.g., spraying, seeding, planting, harvesting, etc.).

In still further embodiments, the agricultural prescription instruction sets may be displayed in a display device such as the output device 124 of FIG. 1 or the output device 184 of FIG. 1. In this way, the present techniques advantageously allow a person of ordinary skill in the art to visualize the interventions that the present techniques recommend to improve the prioritized management of the one or more agricultural fields, based on the feature-based classifications generated by the trained machine learning model, as further analyzed by the rule sets and/or mechanistic crop growth model(s). By visualizing the recommended prioritized management, the agrilytics company is able to effectively communicate a management plan to a grower, and the grower is able to visually understand the planned management priorities.

ADDITIONAL CONSIDERATIONS

The following considerations also apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

It should also be understood that, unless a term is expressly defined in this patent using the sentence "As used herein, the term" "is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of ordinary skill in the art will appreciate still additional alternative structural and functional designs for implementing the concepts disclosed herein, through the principles disclosed herein. Thus, while particular embodiments and applications have been illustrated and described, it is to be understood that the disclosed embodiments are not limited to the precise construction and components disclosed herein. Various modifications, changes and variations, which will be apparent to those of ordinary skill in the art, may be made in the arrangement, operation and details of the method and apparatus disclosed herein without departing from the spirit and scope defined in the appended claims.

What is claimed:

1. A computer-implemented method for prioritizing management of a set of one or more agricultural fields, comprising:
    training a machine learning model by analyzing historical machine data corresponding to one or more agricultural fields;
    receiving, from an agricultural implement, machine data corresponding to one or more agricultural fields, the machine data including one or more sensor measurements;
    classifying the machine data corresponding to one or more agricultural fields using a trained random forest model;
    generating one or more agricultural prescription instruction sets by analyzing the classified machine data using one or more rule sets, wherein the analyzing includes generating an interventions dependency graph, the graph including a plurality of nodes each representing a respective intervention and the graph ordered according to a priority sequence for performing the respective interventions in the one or more agricultural fields; and
    performing the one or more agricultural prescription instruction sets.

2. The computer-implemented method of claim 1, wherein the machine data corresponds to a plurality of 8.5-meter hexagrids.

3. The computer-implemented method of claim 1, wherein receiving the machine data corresponding to the one or more agricultural fields includes an agricultural implement sampling the one or more agricultural fields using a soil probe.

4. The computer-implemented method of claim 1, further comprising:
    resolving one or more interdependencies of the one or more agricultural prescription sets.

5. The computer-implemented method of claim 1, further comprising:
    simulating the effect of one or more agricultural treatments with respect to the one or more agricultural fields.

6. The computer-implemented method of claim 1, further comprising:
    generating an enterprise report including the one or more agricultural prescription instruction sets.

7. The computer-implemented method of claim 1, further comprising:
    generating an agricultural prescription including the one or more agricultural prescription instruction sets, and
    performing the agricultural prescription by executing the one or more agricultural prescription instruction sets of the agricultural prescription in an implement control module of an agricultural implement.

8. A computing system comprising:
    one or more processors; and
    one or more memories storing instructions that, when executed by the one or more processors, cause the computing system to:
    train a machine learning model by analyzing historical machine data corresponding to one or more agricultural fields;
    receive, from an agricultural implement, machine data corresponding to one or more agricultural fields, the machine data including one or more sensor measurements;
    classify the machine data corresponding to one or more agricultural fields using a trained random forest model;
    generate one or more agricultural prescription instruction sets by analyzing the classified machine data using one or more rule sets, wherein the analyzing includes generating an interventions dependency graph, the graph including a plurality of nodes each representing a respective intervention and the graph ordered according to a priority sequence for performing the respective interventions in the one or more agricultural fields; and
    perform the one or more agricultural prescription instruction sets.

9. The computing system of claim 8, wherein the machine data corresponds to a plurality of 8.5-meter hexagrids.

10. The computing system of claim 8, the one or more memories including further instructions that, when executed by the one or more processors, cause the computing system to:
    sample the one or more agricultural fields using a soil probe of an agricultural implement.

11. The computing system of claim 8, the one or more memories including further instructions that, when executed by the one or more processors, cause the computing system to:
    resolve one or more interdependencies of the one or more agricultural prescription sets.

12. The computing system of claim 8, the one or more memories including further instructions that, when executed by the one or more processors, cause the computing system to:

simulate the effect of one or more agricultural treatments with respect to the one or more agricultural fields.

13. The computing system of claim 8, the one or more memories including further instructions that, when executed by the one or more processors, cause the computing system to:

generate an enterprise report including the one or more agricultural prescription instruction sets.

14. The computing system of claim 8, the one or more memories including further instructions that, when executed by the one or more processors, cause the computing system to:

generate an agricultural prescription including the one or more agricultural prescription instruction sets, and perform the agricultural prescription by executing the one or more agricultural prescription instruction sets of the agricultural prescription in an implement control module of an agricultural implement.

15. A non-transitory computer readable medium containing program instructions that when executed, cause a computer to:

train a machine learning model by analyzing historical machine data corresponding to one or more agricultural fields;

receive, from an agricultural implement, machine data corresponding to one or more agricultural fields, the machine data including one or more sensor measurements;

classify the machine data corresponding to one or more agricultural fields using a trained random forest model;

generate one or more agricultural prescription instruction sets by analyzing the classified machine data using one or more rule sets, wherein the analyzing includes generating an interventions dependency graph, the graph including a plurality of nodes each representing a respective intervention and the graph ordered according to a priority sequence for performing the respective interventions in the one or more agricultural fields; and perform the one or more agricultural prescription instruction sets.

16. The non-transitory computer readable medium of claim 15, wherein the machine data corresponds to a plurality of 8.5-meter hexagrids.

17. The non-transitory computer readable medium of claim 15, containing further program instructions that when executed, cause a computer to:

sample the one or more agricultural fields using a soil probe of an agricultural implement.

18. The non-transitory computer readable medium of claim 15, containing further program instructions that when executed, cause a computer to:

resolve one or more interdependencies of the one or more agricultural prescription sets.

19. The non-transitory computer readable medium of claim 15, containing further program instructions that when executed, cause a computer to:

simulate the effect of one or more agricultural treatments with respect to the one or more agricultural fields.

20. The non-transitory computer readable medium of claim 15, containing further program instructions that when executed, cause a computer to:

generate an agricultural prescription including the one or more agricultural prescription instruction sets, and perform the agricultural prescription by executing the one or more agricultural prescription instruction sets of the agricultural prescription in an implement control module of an agricultural implement.

\* \* \* \* \*